(12) United States Patent
Szczykutowicz et al.

(10) Patent No.: US 11,311,264 B2
(45) Date of Patent: Apr. 26, 2022

(54) COMPUTED TOMOGRAPHY MACHINE FOR INTERVENTIONAL USE

(71) Applicant: Wisconsin Alumni Research Foundation, Madison, WI (US)

(72) Inventors: Timothy Szczykutowicz, Madison, WI (US); Emily Knott, Grafton, WI (US); Fred Lee, Madison, WI (US)

(73) Assignee: Wisconsin Alumni Research Foundation, Madison, WI (US)

( * ) Notice: Subject to any disclaimer, the term of this patent is extended or adjusted under 35 U.S.C. 154(b) by 0 days.

(21) Appl. No.: 17/018,783

(22) Filed: Sep. 11, 2020

(65) Prior Publication Data

US 2022/0079541 A1 Mar. 17, 2022

(51) Int. Cl.
*A61B 6/00* (2006.01)
*A61B 6/03* (2006.01)
*A61B 6/10* (2006.01)
*A61B 6/12* (2006.01)

(52) U.S. Cl.
CPC ............ *A61B 6/5282* (2013.01); *A61B 6/032* (2013.01); *A61B 6/107* (2013.01); *A61B 6/12* (2013.01); *A61B 6/4078* (2013.01); *A61B 6/461* (2013.01); *A61B 6/527* (2013.01); *A61B 6/542* (2013.01)

(58) Field of Classification Search
CPC ......... A61B 6/032; A61B 34/20; A61B 34/10; A61B 2034/2055; A61B 34/25; A61B 6/5282; A61B 6/12; A61B 6/527; A61B 6/461; A61B 6/107; A61B 6/542; A61B 6/4078
See application file for complete search history.

(56) References Cited

U.S. PATENT DOCUMENTS

| 10,441,239 B2 | 10/2019 | Abe |
| 2004/0068171 A1 | 4/2004 | Ruimi |
| 2015/0245804 A1* | 9/2015 | Kieft ..................... A61B 6/584 378/147 |

(Continued)

FOREIGN PATENT DOCUMENTS

| EP | 0819407 A1 | 1/1998 |
| EP | 0860144 A2 | 8/1998 |

OTHER PUBLICATIONS

Kilian-Meneghin et al. "Evaluation of methods of displaying the real-time scattered radiation distribution during fluoroscopically guided interventions for staff dose reduction." In Medical Imaging 2018: Physics of Medical Imaging, vol. 10573, p. 1-15. International Society for Optics and Photonics, 2018. New York; US.

(Continued)

*Primary Examiner* — Courtney D Thomas
(74) *Attorney, Agent, or Firm* — Boyle Fredrickson, S.C.

(57) ABSTRACT

A computed tomography machine suitable for interventional procedures provides partial scans displaced about the patient away from the physician position to substantially reduce Compton scattering received by the physician. A modeling of patient dose accounting for the presence of shielding, different physician characteristics, patient positions, and probe position may be accomplished to affect a trade-off between these various factors optimized for interventional or similar procedures where a nonpatient must be close to the scanner during operation.

16 Claims, 5 Drawing Sheets

(56) References Cited

U.S. PATENT DOCUMENTS

2016/0095567 A1     4/2016   Tachikawa
2016/0120485 A1*   5/2016   Sakai ..................... A61B 6/461
                                                                                                                     378/16

OTHER PUBLICATIONS

PCT International Search Report for PCT/US2021/049550 dated Dec. 29, 2021.

* cited by examiner

COMPUTED TOMOGRAPHY MACHINE FOR INTERVENTIONAL USE

STATEMENT REGARDING FEDERALLY SPONSORED RESEARCH OR DEVELOPMENT

CROSS REFERENCE TO RELATED APPLICATION

BACKGROUND OF THE INVENTION

The present invention relates to x-ray computed tomography (CT) devices and in particular to an x-ray CT machine improving the ability of the physician to remain near the patient during interventional procedures.

Computer tomography (CT) provides an x-ray image, for example, of a patient, mathematically reconstructed from a number of x-ray attenuation measurements (projections). The projections used to reconstruct this slice are taken over a range of angles along a transverse plane edgewise through the slice perpendicular to a superior-inferior axis of the patient and form a tomographic projection set. In a basic form, the reconstructed tomographic image may present a cross-sectional image of the patient as if one were viewing a transverse slice extracted from the patient.

In one common form, the x-ray CT machine provides for a gantry rotatable about a center opening or bore for receiving the patient. The gantry supports an x-ray tube and x-ray detector in opposition about the bore to project and receive a fan beam lying within a slice in the transverse plane of the gantry. The gantry then rotates about the patient to obtain the various projections needed for the tomographic projection set. Other CT designs may eliminate the rotating gantry in favor of a fixed circular array of x-ray sources and detectors.

Commonly, projections of the tomographic projection set are obtained over a range of 360° of rotation to minimize image artifacts in the reconstruction process. Alternatively, it is known to use "partial" scans over an angular range equal to 1800 plus the angle subtended by the fan beam of x-rays from the x-ray tube as received by the detector. These partial scans take advantage of the fact that x-ray attenuation along a line through the patient will be similar when taken in directions differing by 180 degrees. Partial scans are frequently used when high-speed imaging is required, for example, in cardiac imaging, because they reduce the amount of time required for gantry motion allowing for faster slice acquisition. The reduction in acquired image data, such as may affect image signal-to-noise ratio, may be offset by increasing the x-ray fluence or x-ray tube current.

CT imaging can be extremely helpful in interventional procedures, for example, guiding a biopsy needle to an internal lesion. Such CT "fluoroscopy" has an advantage over conventional x-ray fluoroscopy in that it provides the physician with a view of a slice isolated from adjacent tissue. In this respect, CT fluoroscopy eliminates the ambiguity that would be present in a standard x-ray projection image (per conventional x-ray fluoroscopy) where different tissue planes are superimposed (anatomical overlay). Anatomical overlay, for example, might suggest that a biopsy needle were in a lesion when in fact the lesion and biopsy needle were in different overlying but separated planes.

A significant disadvantage to CT fluoroscopy with respect to standard fluoroscopy, however, is the high dose delivered by a CT machine which results in increased exposure from scattered radiation to the physician performing the interventional procedure. In order to reduce the effect of such scattered radiation in CT fluoroscopy, many interventional radiologists exit the room after each incremental positioning of the biopsy needle to take an additional tomographic scan before returning again to the room. This process of incrementally positioning the biopsy needle and taking an additional scan from outside of the CT room is repeated many times, greatly increasing the procedure time and/or encouraging coarser increments of needle movement.

SUMMARY OF THE INVENTION

The present inventors have recognized that scattered radiation to the physician during a tomographic scan can be substantially reduced by preferentially directing x-ray radiation toward the physician from the far side of the patient in a partial scan. While preferentially directing the x-rays toward the physician may seem counterintuitive, this approach greatly reduces physician dose as a result of three combined factors including: (1) the substantially higher x-ray flux on the side of the patient through which the beam enters; (2) the dominance of Compton scattering which results in substantial backscatter relative to forward scatter; and (3) the effective shielding mass of the patient with respect to forward scatter.

By adjusting the radiation exposure pattern in this way, physician dose can be reduced by over 30% without substantial degradation in the image. Additional dose reduction techniques can be added to this approach to obtain even more dose reductions making CT fluoroscopy even more amenable to continued physician presence during the scanning process.

More specifically then, in one embodiment, the invention provides a computed tomography system having an x-ray source for projecting a beam of x-rays toward a patient at different angles about a patient over an angular range and an x-ray detector providing multiple detector elements positioned to measure attenuation of the x-rays of the beams, by the patient, passing through the patient at the different angles over the angular range. An electronic computer communicating with the x-ray source and x-ray detector operates to: (a) receive location information about a location of a non-patient proximate to the x-ray computed tomography system; (b) based on the location information, control the x-ray source to preferentially direct x-rays through the patient toward the location to acquire a tomographic projection set of x-ray attenuation by the patient; and (c) reconstruct a tomographic image from measured attenuation of the preferentially directed x-rays.

It is thus a feature of at least one embodiment of the invention to provide an x-ray CT system that tailors the x-ray delivery to a known location of a non-patient in proximity to the CT machine to permit more time-efficient interventional procedures or the ability of caregivers to remain "bedside" to the patient, for example, parents with children being scanned.

The x-ray source may be controlled to preferentially direct x-rays to the patient by reducing x-ray fluence in an exclusion angular range opposite a preferential angular range where the preferential angular range is centered about a non-vertical angle.

It is thus a feature of at least one embodiment of the invention to place the entrance point of the x-ray beam opposite the physician so that maximum Compton backscatter caused by the high flux at the entrance point is oriented away from the physician.

The preferential angular range may be less than 300°.

It is thus a feature of at least one embodiment of the invention to enlist partial scan reconstruction techniques to limit entrance dose backscatter on the physician side of the patient.

The location information may be received from a sensor providing real-time sensing of nonpatient location.

It is thus a feature of at least one embodiment of the invention to both simplify CT machine set up for interventional or similar procedures and to provide independent corroboration of nonpatient position, for example, when physician or patient positioning must be changed dynamically during the interventional procedure.

The information about the location of the nonpatient may be derived from a confirmation of a proposed location of the nonpatient.

It is thus a feature of at least one embodiment of the invention to enlist the CT machine in recommending physician location and/or physician and patient locations.

The electronic computer may output an estimate of scatter dose received at the location according to the preferentially directed x-rays.

It is thus a feature of at least one embodiment to provide important dose information to the nonpatient individual for use in planning and in evaluating different imaging options, including recommending locations of shields or allowing those locations to be assessed.

In some embodiments, the system may include a radiation sensor positioned proximate to the location for determining an actual scatter dose and the electronic computer may compare the actual scatter dose to the estimate of scatter dose to provide a warning if these differ by more than a predetermined amount.

It is thus a feature of at least one embodiment of the invention to provide confirmation of scatter calculations and the ability to respond to dynamic situations during the imaging process, for example, the movement of the patient, shields, etc.

In some embodiments, the x-ray computed tomography system further includes a display visually confirming the location. For example, the display may provide at least one illuminated indicator positioned proximate to the location to indicate, through illumination and its proximity, the location information.

It is thus a feature of at least one embodiment of the invention to provide readily accessible information about the underlying assumptions covering the delivery of radiation.

The electronic computer may further receive patient positioning information indicating a positioning of the patient in the CT scanner and may preferentially direct x-rays through the patient toward the location based on the location information and patient positioning information.

It is thus a feature of at least one embodiment of the invention to provide improved operator dose reduction by better understanding patient position and to correct what may be otherwise mistaken assumptions about patient positioning and centering.

The preferential direction of x-rays may be based on location information, and the patient positioning information may minimize a joint function of patient dose and nonpatient dose at the location.

It is thus a feature of at least one embodiment of the invention to permit flexible trade-offs that both reduce nonpatient scattered radiation and dose to the patient.

In some embodiments, the electronic computer further receives information describing a location of a patient-inserted probe and preferentially directs x-rays through the patient toward the location based on the location information and the location of the patient-inserted probe to reduce probe-induced image artifacts.

It is thus a feature of at least one embodiment of the invention to provide a multidimensional optimization of x-ray delivery that maximizes positional information on a biopsy probe or the like.

The electronic computer may further receive information about a location of an x-ray shield proximate to the location and preferentially direct x-rays through the patient toward the location based on location information and shield location.

It is thus a feature of at least one embodiment of the invention to integrate with other scatter protection devices such as shields, aprons, and the like.

The electronic computer may further operate to display a tomographic image of the patient modified by simulated noise according to a selected x-ray fluence of the x-ray source and in this regard may receive an input allowing physician adjustment of the selected x-ray fluence and may further control the x-ray source to provide a fluence matching the selected x-ray fluence during the preferential directing of x-rays through the patient toward the location.

It is thus a feature of at least one embodiment of the invention to further reduce x-ray scatter by minimizing x-ray dose consistent with the narrow task of tracking an interventional probe.

These particular features and advantages may apply to only some embodiments falling within the claims and thus do not define the scope of the invention.

DETAILED DESCRIPTION OF THE PREFERRED EMBODIMENT

Figure 1:
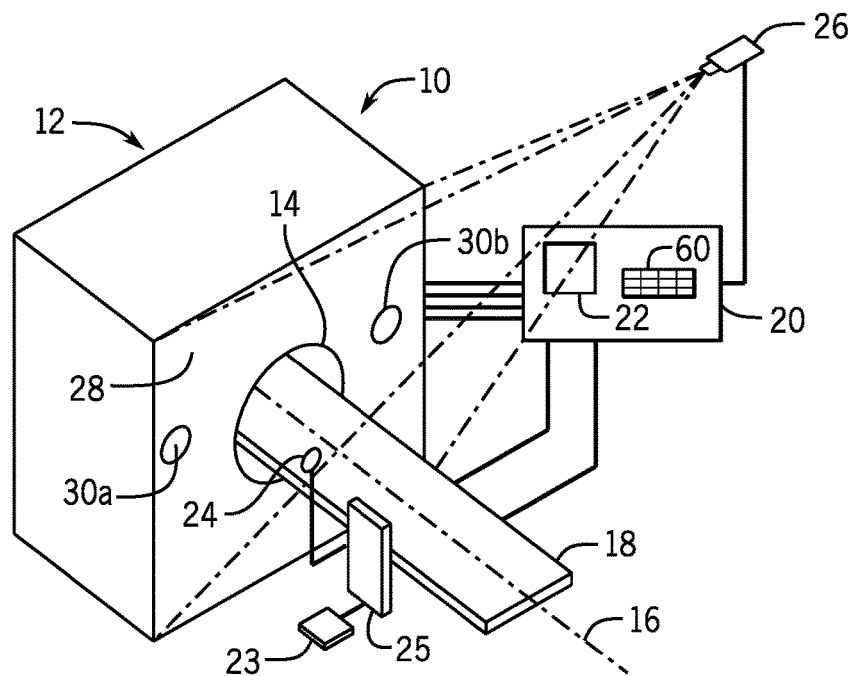
FIG. 1 is a simplified block diagram of a CT machine suitable for use with the present invention and showing a patient positioning table partially inserted into the CT bore, a shield, physician location guidance lights, and a camera used in one embodiment of the invention.

Referring now to FIG. 1, an x-ray CT machine 10 may provide for a scanner 12 having a central bore 14 extending along an axis 16. The central bore 14 may receive a patient (not shown) supported on a radiolucent patient table 18 to be freely positioned within the bore 14. The scanner 12 may be attached to a console 20, for example, providing a graphic display 22 for displaying tomographic images to a physician positioned near the bore 14 during an interventional procedure and providing a keyboard or other user entry device 60 for entering data by the physician as will be discussed below.

Optionally, in the present invention, the console 20 may communicate with an infrared camera 26 positioned to detect nonpatient individuals (such as a physician) adjacent to the bore 14, a foot pedal 23 providing input, for example, to trigger the acquisition of a scan during an interventional procedure, and a radiation sensor 24 that may be used to confirm scatter dose as will be discussed below.

In this embodiment a front face 28 of the scanner 12 outside of the bore 14 may provide for illuminated displays 30*a* and 30*b* positioned to the left and right of the bore 14 that may be illuminated, for example, with red or green or with a printed message to indicate the intended location of the physician during the interventional procedure.

One or more shields 25 may also be associated with the scanner 12, for example, including a transparent x-ray shield suspended from ceiling tracks providing a leaded glass or leaded acrylic panel which may be attached to location sensors to provide location information. Alternative or additional shields 25 may include body worn shields such as lead aprons and the like.

Figure 2:
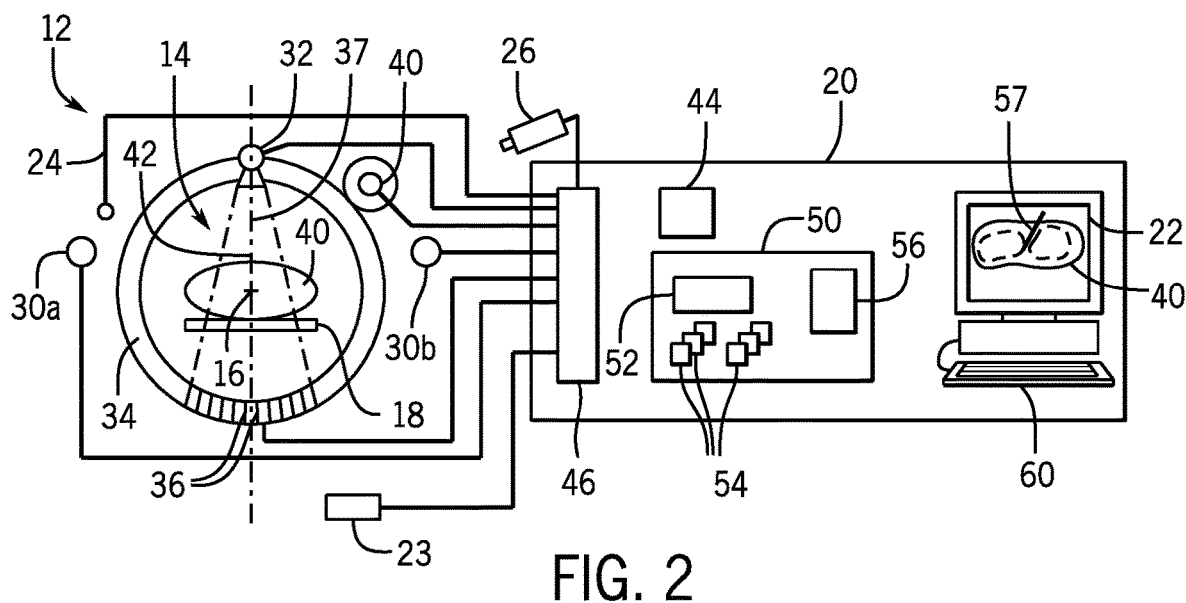
FIG. 2 is a block diagram of the principal components of the CT machine of FIG. 1 showing an internal rotating gantry holding an x-ray tube and detector array and depicting a computer having programs used for the reconstruction process and implementation of the present invention, the computer such as may be associated with a graphic display terminal for displaying tomographic images for guiding an interventional procedure.

Referring now also to FIG. 2, within a housing of the scanner 12, an x-ray source 32, such as an x-ray tube, may be mounted on a ring gantry 34 to project a fan x-ray beam 37 inwardly toward and perpendicular to axis 16. The fan x-ray beam 37 may pass through a patient 40 on the table 18 within the bore 14 to be received by a detector array 36 also mounted on the ring gantry 34. The detector array 36 provides multiple sensor elements to make individual attenuation measurements at a variety of angularly displaced rays along the fan x-ray beam 37 in a slice plane.

The ring gantry 34 is rotatable about the axis 16, for example, by a motor/encoder assembly 41 to change a primary axis 42 of the fan beam 37 to obtain a variety of projections at different angles for tomographic reconstruction as is generally understood in the art. The motor/encoder assembly 41 is controlled from the console 20 to adjust not only the angle of the primary axis 42 but also the range of angles of that axis 42 over which projections will be acquired, typically at regularly spaced angular increments.

The console 20 may include one or more computer processors 44 receiving signals via interface circuitry 46 from the detector array 36, the pedal 23, the camera 26, the dose sensor 24, and any sensors on the shields 25. In addition, the processors 44, via the interface circuitry 46 provide signals to the illuminated displays 30*a* and 30*b* and to the x-ray source 32 to control its current (and hence x-ray flux) generally allowing it to be turned on and off as desired. Via the interface circuitry 46, the processors 44 may also control the motor/encoder assembly 41 to control the angle of acquisitions as discussed above.

The computer processors 44 generally communicate with a memory 50 holding a program 52 for controlling the acquisition of projections as will be discussed below as well as collected image data 54 including one or both of projection sets and images reconstructed from the projection sets by a reconstruction engine 56. The reconstruction engine 56 may, for example, use well-known tomography algorithms such as, filtered back projection or the like.

In addition, the processors 44 may communicate with the graphic display 22 for outputting tomographic images of the patient 40 and a probe 57 such as a biopsy needle being guided during an interventional procedure. Likewise, the processors 44 may receive commands or data from the user entry device 60, for example, a keyboard, trackpad, touchscreen, mouse, or the like.

Figure 3:
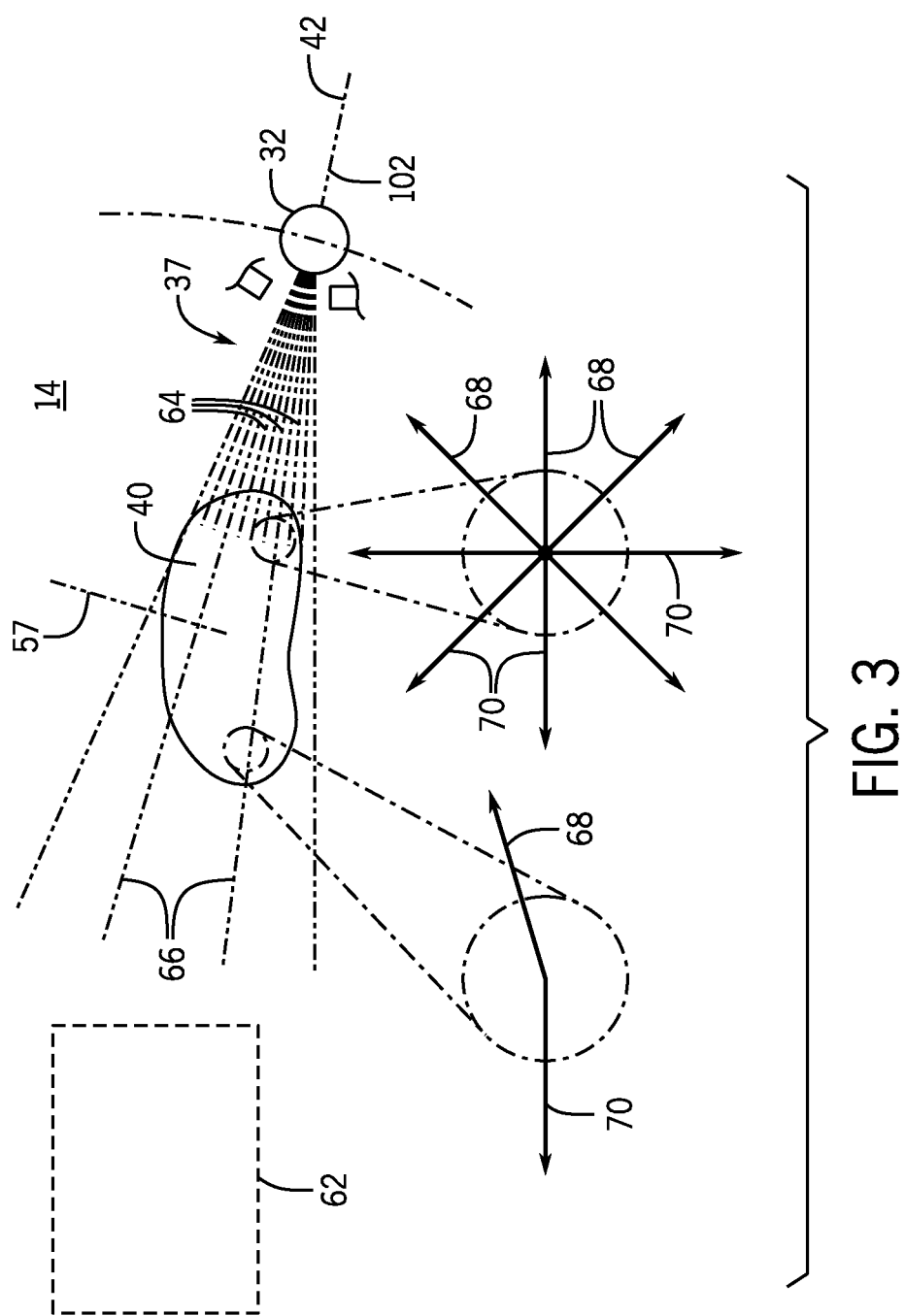
FIG. 3 is a simplified diagram of a patient during acquisition of a projection showing increased flux at the point of entrance of the x-ray beam into the patient and the Compton scattering which produces a substantial amount of backscatter.

Referring now to FIG. 3, when the x-ray source 32 is on the far side of the patient 40 with respect to a physician location 62, the patient 40 receives a high entrance fluence 64 of x-rays in the fan beam 37 which, after attenuation by the patient 40, produces a lower exit fluence 66 of the fan beam 37 exiting the patient 40 in the direction of the physician location 62. Generally, the exit fluence 66 of un-scattered x-rays will be as little as 1/100th that of the entrance fluence 64. The difference between the entrance fluence 64 and exit fluence 66 is the result of scattering and absorption of the x-rays by the tissue of the patient 40.

Figure 4:
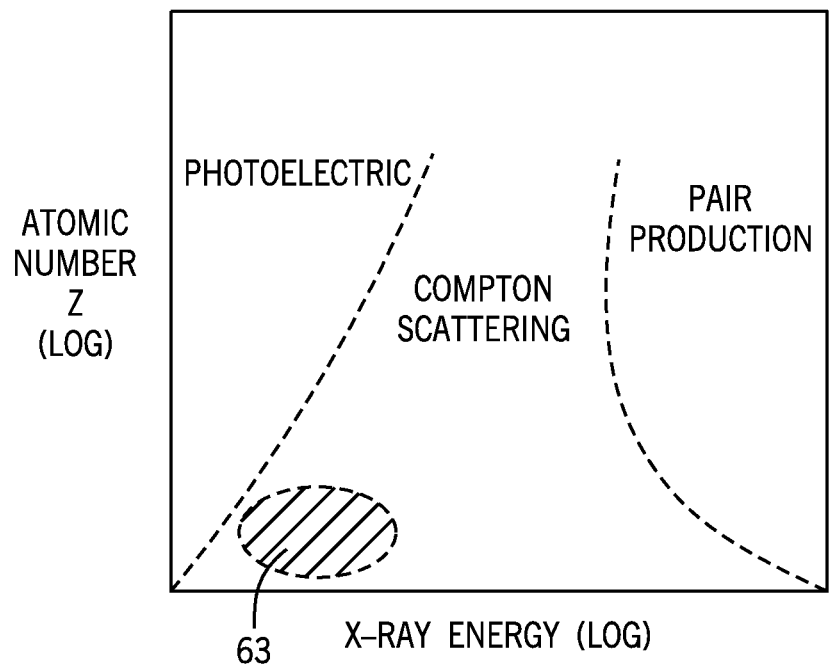
FIG. 4 is a diagram showing regions of photoelectric scattering, Compton scattering, and pair production scattering as a function of imaged material and x-ray energy.
Figure 5:
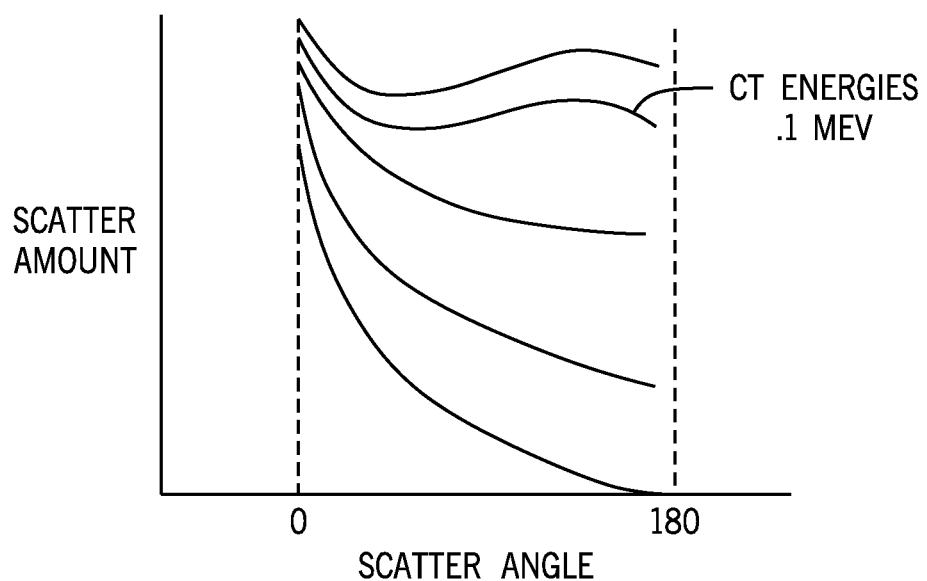
FIG. 5 is a diagram showing Compton scattering as a function of angle at various x-ray energies.

Referring now momentarily to FIG. 4, the type of scattering is highly dependent on the material through which the x-rays are passing (atomic number Z) and the energy of the x-ray beam. For kilovoltage x-ray energies passing through human tissue, the scattering will be localized in the chart of FIG. 4 in a region 63 dominated by Compton scattering. Referring now to FIG. 5, Compton scattering is characterized at the energy levels of diagnostic x-rays as producing substantial backscatter, for example, at angles near to 180 degrees, being a significant portion of all scattered radiation. Scattering at diagnostic imaging energies is usually dominated by the Compton effect, but other interactions such as Rayleigh scattering and the Photoelectric effect are present.

Referring again to FIG. 3, the dominance of Compton scattering thus results in significant backscatter x-rays 68 toward the x-ray source 32 along with forward and side scattered x-rays 70. This scatter pattern combined with the large entrance fluence 64 results in a substantial backscatter dose to a physician or other nonpatient individual standing on the entrance side of the patient 40. In contrast, this high proportion of Compton back scattering of the entrance fluence 64 decreases scatter dosage toward an individual standing at the exit side of the patient 40, a factor, which combined with the lower exit fluence 66 results in very few side scattered x-rays 70 that would be received at the physician location 62. The forward scattered x-rays 70, at the entrance side of the patient 40, are further substantially attenuated by the patient 40.

These factors altogether result in a reduction of over 30% of scatter dose to a nonpatient individual positioned at physician location 62 when the x-ray source 32 is opposite the physician location 62 with respect to the patient 40 and directed in the direction of the physician location 62.

Note generally that the physician location 62 will not be in the slice plane and thus will not receive the un-scattered x-rays of the exit fan beam 37 but only those scattered x-rays that scatter out of the plane of the fan beam. Collimator blades (not shown) forming the fan beam 37 will block direct x-ray transmissions from the x-ray source 32 to the physician location 62. Thus, while it is desired that the x-ray source 30 be primarily directed toward the physician location 62 during image acquisition, this should be understood to describe a general direction rather than a precise alignment.

Figure 6:
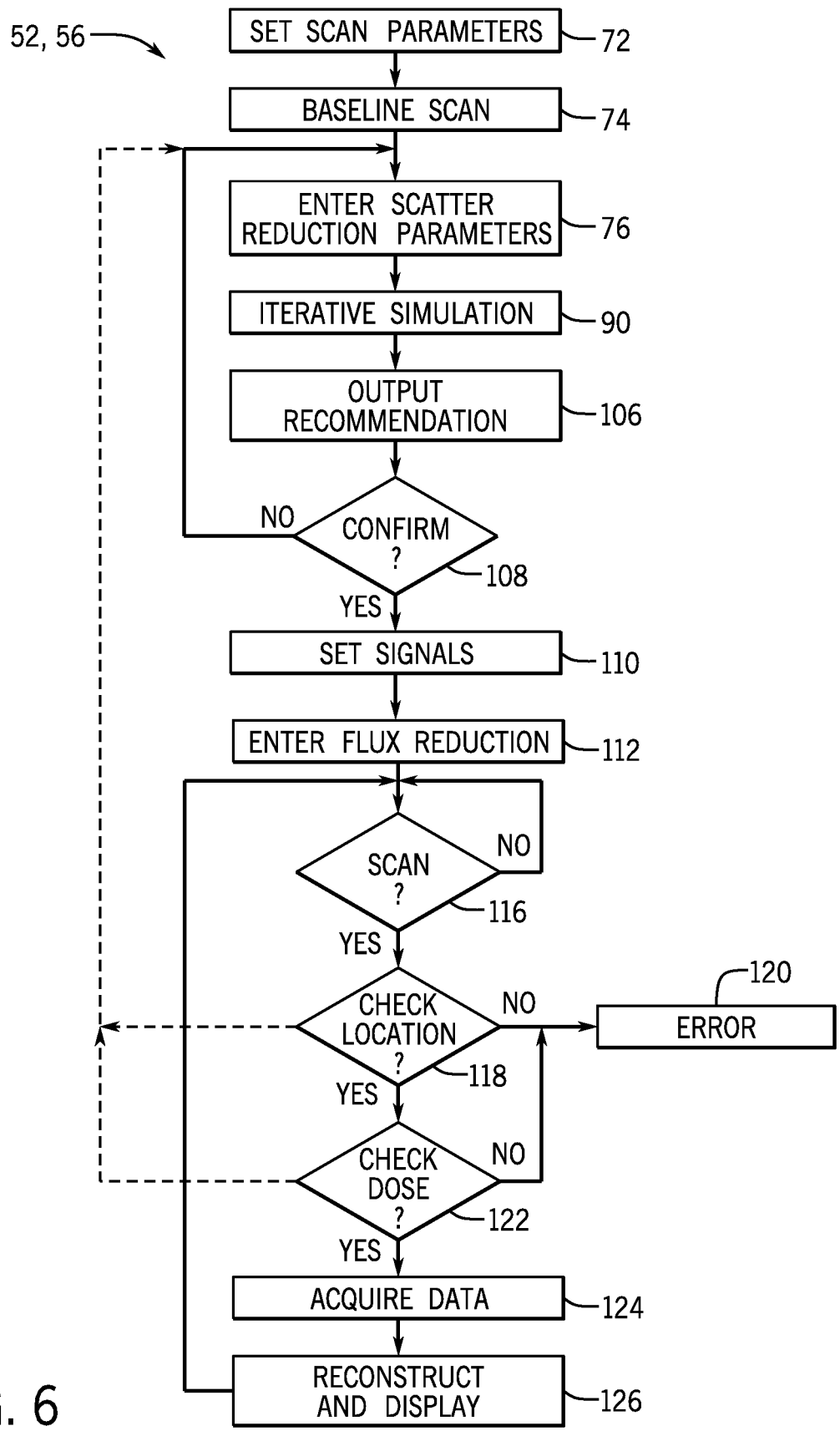
FIG. 6 is a block diagram of the programs executed on the computer of FIG. 2 for acquiring CT images for interventional procedures.

Referring now to FIG. 6, program 52 and reconstruction engine 56 may operate as indicated by process block 72 to receive settings for a CT acquisition of a tomographic projection set including, for example, x-ray tube voltage and x-ray tube current per a standard CT image of the patient of the type that can provide a baseline image. Data for this image may then be acquired as indicated by process block 74 and reconstructed to be displayed on the display console 20. Desirably, this image is obtained at a slice location aligned with the lesion where a biopsy will be taken.

Figure 7:
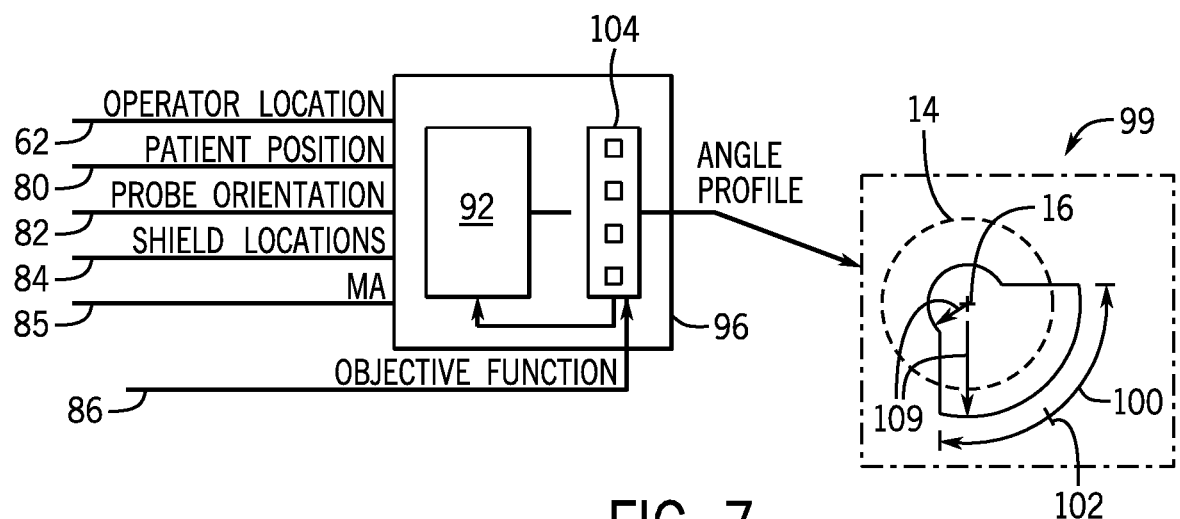
FIG. 7 is a block diagram of an iterative simulation program used for optimizing CT acquisition angle per the program of FIG. 6.

Referring also to FIG. 7, at process block 76 scatter reduction parameters may be entered per the present invention to reduce scattered x-rays received by the physician at the physician location 62.

These parameters may include physician location 62, for example, on the left or right side of the scanner 12, as well as physician specific information, for example, physician height and optionally weighted exposure zones (for example, head, chest, eyes). The weighting allows different maximum dose or dose preference or relative contribution to be designated for these regions, for example, allowing lower dose for the physician's head than the chest region under the assumption that the physician will be wearing x-ray protective gear.

It will be appreciated that the physician location 62 may alternatively be deduced automatically, for example, by image recognition using the camera 26 or inferred from positioning of the console 20 or the pedal 23, or the use of weight-sensitive mats or the like.

In addition, at process block 76, patient location and positioning information 80 may be entered indicating whether the patient is supine or left or right decubitus and the degree to which the patient 40 is centered or not centered within the bore 14. In addition, information about the thickness of the patient at different parts of the patient's body and at different orientations may be provided. This information may be entered manually or may be part of the data entered at process block 72.

At process block 76, orientation and the location of the probe 57 (for example, a biopsy needle) may be entered such as may be used to optimize the reduction of image artifacts caused by the probe 57 during a partial scan as will be discussed below. Finally, locations and dimensions 84 of the shield 25, if any, may be entered as well as shield attenuating properties. In this regard, standard shield types may be available to be selected from a menu or the like and shield location may be indicated and entered either graphically, for example, in a graphic similar to that shown below with respect to FIG. 8 or automatically through the use of sensors attached to the shield 25 and elsewhere in the room to locate the shield respectively.

Optionally, an objective function 86 may be entered, for example, when it is desired to affect a certain trade-off between physician dose, patient dose, and reduction of probe artifacts and the like. Alternatively, a standard default objective function may be used or selected. In a simple case, the objective function may establish a weighted summation of doses in different regions of the patient 40 and physician in physician location 62 and of artifact severity. The weights may be selected by the physician or established according to empirically derived guidelines.

Figure 8:
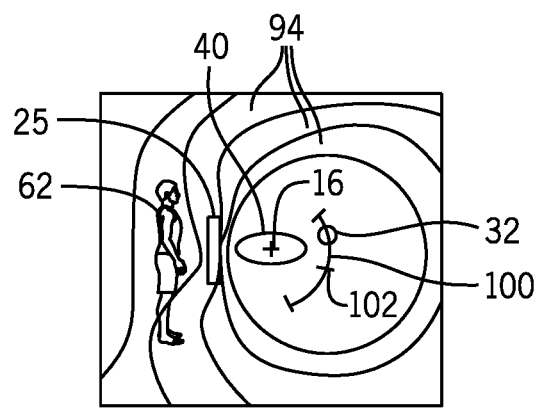
FIG. 8 is a depiction of iso-dose lines from a simulation of the x-ray's scatter dose used in the present invention.

Referring now also to FIG. 8, at process block 90 a simulation engine 92 may receive this information entered at process block 76 and may perform a simulation of the scatter dose generated during imaging of the patient 40 under various scenarios, for example, using a Monte Carlo simulation or the like to provide a set of iso-dose lines or zones 94. These iso-dose zones 94 of each scenario will be associated with assumptions about a given angular range 100 of the partial scan of the x-ray source 32 with respect to the patient 40 and a center point 102 of the angular range 100. Generally, the angular range 100 will be set to a partial scan equal to 180 degrees or more and typically 180 degrees plus the fan beam angle and normally less than 300 degrees. Each simulation may also evaluate image artifacts generated by the high Z material of the probe 57. For each scenario, the dose of the iso-dose regions defined by iso-dose zones 94 will be integrated over the zones of the physician location 62 to determine a cumulative dose in each of the defined zones. This dose is also weighted according to the previously defined weighting values to provide a "goodness value" with respect to minimizing the objective function.

The center point 102 and optionally the angular range 100 may then be varied by an iterator 104 and a new simulation performed until iso-dose lines 94, cumulative dose, and goodness values have been obtained for a variety of different angular ranges 100 and center points 102. The iterator 104 then selects the center point 102 and angular range 100 (with the constraints on obtaining a projection set discussed above) together defining a preferential angular range and providing the highest "goodness."

The iterator 104 may then output the selected angular range 100 and center point 102 of a partial scan 99 as indicated by process block 106 of FIG. 4. While the particular value of the center point 102 will depend on the scanner 12, the physician location 62 and a variety of other factors, generally the center point 102 will be positioned opposite the patient 40 with respect to the physician location 62 at an angular range between 20 degrees above horizontal and 85 degrees below horizontal. In a simplest case, the x-ray source 32 will be activated only during this preferential angular range and not in an exclusion angular range subtending the remainder of 360 degrees about the patient 40. However, the invention contemplates that the electrical current level 109 to the x-ray tube of the x-ray source 32 may be nonzero in the exclusion range so long as it is substantially reduced with respect to the preferential angular range (typically less than one third of the amperage level in the range 100 and in many cases less than $\frac{1}{10}$).

It will be appreciated that the iterator 104 need not be constrained to iteration with respect to the center point 102 (and angular range 100) but may also iterate with respect to different patient positions, for example, shifting the patient 40 within the bore 14 laterally and vertically and moving the position of the patient 40 experimentally between supine and the decubitus positions, for example, providing recommendations for such positionings in the optimization process. The x-ray tube current level 109 during the partial scan 99 also need not be constant but may be iteratively adjusted to promote the desired trade-offs between scatter reduction and image quality. These additional dimensions of optimizing may be made computationally tractable by employing several standard milliamp variations and iterating among those to find the best solution, for example, boosting the milliamp level when the likely scatter will be received by a shield 25.

The iterator 104 may also be enlisted to propose alternative locations of shielding 25 or the addition of shields 25, for example, by considering one or more standard shield situations even when a shield 25 is not initially contemplated. For example, the iterator 104 may present scenarios that provide additional reduction in dose, such as proposing the addition of a lead skirt to the table or a movement of the physician location closer to the patient's head to reduce the dose by some quantified amount (e.g. 5%).

At process block 108, the scanner settings and assumptions used for the settings produced by the simulator of process block 90 must be approved by the physician. In this respect, the invention contemplates that the scanner 12 may assume a default physician location 62, for example, and that confirmation of this default position operates as location information input.

At process block 110, once a physician location 62 has been identified, displays 30a and 30b on the scanner 12 may be illuminated to indicate proper location of the physician; for example, a green lamp or an illuminated sign denoting "physician location" may be placed on the side of the scanner 12 of the physician location 62 and a red lamp or sign indicating "do not stand here" placed on the opposite side of the bore 14. It will be appreciated that other indicia may be used including a localized indication on the display 22 or a crosshairs or the like projected by laser or other means on the floor. This latter approach allows the optimization process to recommend different locations to the physician for reduced dose. Placement of the console 20 or pedal 23 may also be used to enforce proper physician location.

At process block 112, the physician may undertake additional steps for reducing x-ray dosage including selecting a tighter x-ray fan beam collimation to make a thinner fan beam (for example, 20 mm versus 40 mm), activating conventional automatic exposure control that reduces x-ray fluence for thinner projections through the patient 40 depending on projection angle, and additional spectral filtration, all which augment the present invention's selection of beam angles and x-ray flux.

Figure 9:
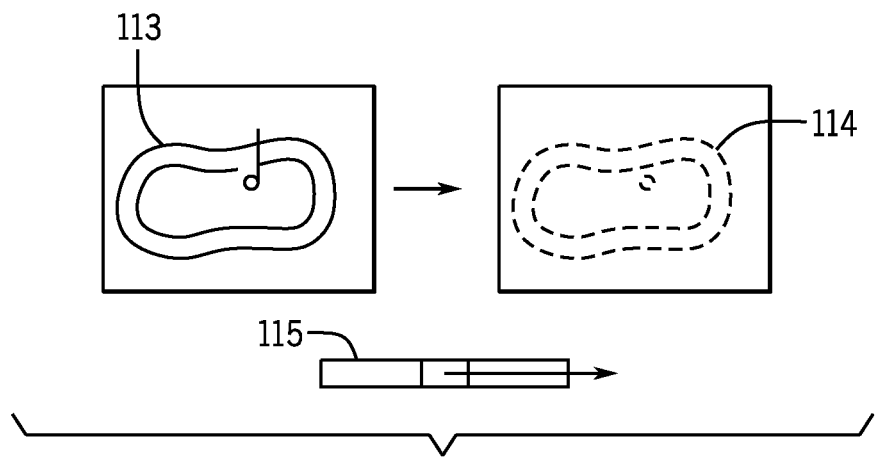
FIG. 9 is a depiction of a display on the graphic display terminal showing an acquired CT image and a simulation of that image with reduced x-ray flux allowing an interactive setting of flux rates by the physician.

Referring now also to FIG. 9, in conventional practice, the x-ray tube current level 109 (milliamperes) will be boosted during a partial scan relative to a full scan to maintain comparable imaging quality; however, in the present invention where the motivation is guidance of a probe, this high level of image quality need not be retained but can be further reduced to reduce physician scatter dosage. Specifically, the physician may adjust the x-ray tube current level 109 to a minimum level necessary for proper guidance of the interventional probe or the like. In one embodiment, the survey scan 113 acquired at process block 74 or a later scan may be displayed on display 22 and the physician given an interactive slider tool 115, for example, implemented on the user entry device 60 to interactively simulate a reduction in the x-ray tube current 109 producing a simulated degraded image 114 based on the survey image that provides guidance of the likely decreased signal-to-noise ratio in the acquired image under such a flux reduction. This simulation may be produced, for example, following the teachings of N Bevins, T Szczykutowicz, M P Supanich, A Simple Method for Simulating Reduced-Dose Images for Evaluation of Clinical CT Protocols," Medical Physics 40 (6 Part 26), 437-437. The ultimately selected x-ray tube current level 109 will then be used for subsequent acquisitions overwriting those originally selected at process block 72.

Upon completion of the above steps, at decision block 116, the program waits for a scan command from the physician, for example, by activating foot pedal 23. At process block 118, confirmation that the physician is in the physician location 62 may be made, for example, using the infrared camera 26, a pressure footpad (not shown), or other technique. If the physician or other nonpatient individual is not properly located or there are additional individuals in the area of the CT scatter, an error condition may be indicated per process block 120, for example, providing a warning tone and indication of the error on the display 22 normally used for providing the tomographic images. Further scanning may be stopped until the error is resolved. Alternatively, an alternate new location may be input at process block 76 and the radiation delivery adjusted according to the new position.

At this point the scanner 12 may output on the display 22 a previously calculated expected dose received by the physician on a per image basis, cumulative dose received so far, and anticipated dose for a previously estimated number of images required for the interventional procedure. This output may be in the form of dose numbers (quantitative), may depict iso-dose lines as shown in FIG. 8, or may be expressed as a percentage of a particular limit, for example, of a typical fluoroscopy procedure, or in comparison to a conventional scan, either graphically or numerically.

Based on these values, on each scan completion the program proceeds to decision block 122 to check the cumulative dose received so far during scans by the physician as entered at process block 76 to ensure that the dose limits have not been exceeded. If the dose limits have been exceeded, the program enters the error state of process block 120 discussed above. Optionally, as indicated by a dotted line in FIG. 6, this information can be used to allow dynamic adjustment of the planning process by returning to process block 76 to adjust the parameters.

Also, at decision block 118, data can be collected from one or more sensors 24 from the previous scan to confirm that the predicted dose conforms to the actual dose received at the physician location 62 or at some proxy location within a predetermined tolerance. A difference between sensor measurements and calculated measurements of more than a certain amount will produce an error condition at process block 120 or return to process block 76 for reconsideration of the scatter reduction parameters.

Otherwise at process block 124, slice image data is acquired during which the x-ray source location moves throughout angular range 100 centered at center point 102 about the patient 40 to acquire a tomographic projection of attenuation measurements along multiple rays of the fan beam 37 with the x-ray source 32 at different locations. Typically, as noted, the angular range 100 will be greater than 1800 and normally at least 180° plus the fan beam angle being the angle subtended by the fan beam 37 within the scanning plane. More generally, a tomographic projection set will be the necessary projections to acquire a clinically meaningful computed tomography image of the patient 40.

The reconstruction may then be accomplished by the reconstruction engine 56 as indicated by process block 126 and this process looped to allow repeated acquisitions of tomographic slice images to guide the interventional procedure without the need for the physician to leave the room.

Early studies of this technique have indicated that the scatter dose received by the physician can be reduced by over 30% with no loss of image quality eliminating the need for the physician to exit from the proximity of the CT machine during the scanning process.

The present invention is applicable to a wide variety of CT architectures including those with a rotating or fixed gantry. As noted above, the input of physician position required for the simulation may be either direct, for example, using a camera or entry by the physician or indirect through a recommendation process which is then approved or confirmed by the physician implicitly or actually so that physician location can be used to determine the x-ray dose pattern.

While the present invention is primarily directed toward assisting healthcare professionals in interventional procedures, it will also be appreciated that it can be extended to the use of medical assistants or parents, for example, for pediatric patients and the like, and may include calculations for multiple individuals.

Certain terminology is used herein for purposes of reference only, and thus is not intended to be limiting. For example, terms such as "upper", "lower", "above", and "below" refer to directions in the drawings to which reference is made. Terms such as "front", "back", "rear", "bottom" and "side", describe the orientation of portions of the component within a consistent but arbitrary frame of reference which is made clear by reference to the text and the associated drawings describing the component under discussion. Such terminology may include the words specifically mentioned above, derivatives thereof, and words of similar import. Similarly, the terms "first", "second" and other such numerical terms referring to structures do not imply a sequence or order unless clearly indicated by the context.

When introducing elements or features of the present disclosure and the exemplary embodiments, the articles "a", "an", "the" and "said" are intended to mean that there are one or more of such elements or features. The terms "comprising", "including" and "having" are intended to be inclusive and mean that there may be additional elements or features other than those specifically noted. It is further to be understood that the method steps, processes, and operations described herein are not to be construed as necessarily requiring their performance in the particular order discussed or illustrated, unless specifically identified as an order of performance. It is also to be understood that additional or alternative steps may be employed.

References to "a microprocessor" and "a processor" or "the microprocessor" and "the processor," can be understood to include one or more microprocessors that can communicate in a stand-alone and/or a distributed environment(s), and can thus be configured to communicate via wired or wireless communications with other processors, where such one or more processor can be configured to operate on one or more processor-controlled devices that can be similar or different devices. Furthermore, references to memory, unless otherwise specified, can include one or more processor-readable and accessible memory elements and/or components that can be internal to the processor-controlled device, external to the processor-controlled device, and can be accessed via a wired or wireless network.

It is specifically intended that the present invention not be limited to the embodiments and illustrations contained herein and the claims should be understood to include modified forms of those embodiments including portions of the embodiments and combinations of elements of different embodiments as come within the scope of the following claims. All of the publications described herein, including patents and non-patent publications, are hereby incorporated herein by reference in their entireties To aid the Patent Office and any readers of any patent issued on this application in interpreting the claims appended hereto, applicants wish to note that they do not intend any of the appended claims or claim elements to invoke 35 U.S.C. 112(f) unless the words "means for" or "step for" are explicitly used in the particular claim.

What we claim is:

1. An x-ray computed tomography system comprising:
   an x-ray source for projecting a beam of x-rays toward a patient at different angles about a patient over an angular range;
   an x-ray detector providing multiple detector elements positioned to measure attenuation of the x-rays of the beams by the patient passing through the patient at the different angles over the angular range; and
   an electronic computer communicating with the x-ray source and x-ray detector to:
   (a) receive location information about a location of a nonpatient proximate to the x-ray computed tomography system;
   (b) perform a scatter simulation based on patient information and the received location;
   (c) based on the scatter simulation, control the x-ray source to preferentially direct x-rays through the patient toward the location to acquire a tomographic projection set of x-ray attenuation by the patient; and
   (d) reconstruct a tomographic image from measured attenuation of the preferentially directed x-rays.

2. The x-ray computed tomography system of claim 1 wherein the x-ray source is controlled to preferentially direct x-rays to the patient by reducing x-ray fluence in an exclusion angular range opposite a preferential angular range and wherein the preferential angular range is centered about a non-vertical angle.

3. The x-ray computed tomography system of claim 2 wherein the preferential angular range is less than 300°.

4. The x-ray computed tomography system of claim 1 wherein the different angles about the patient intersect a common axis and the x-ray source projects a fan beam of radiation in a plane substantially perpendicular to the common axis.

5. The x-ray computed tomography system of claim 1 wherein the location information is received from a sensor providing real-time sensing of nonpatient location.

6. The x-ray computed tomography system of claim 1 wherein the information about the location of the nonpatient is from a confirmation of a proposed location of the nonpatient.

7. The x-ray computed tomography system of claim 1 wherein the x-ray computed tomography system further includes a display visually confirming the location.

8. The x-ray computed tomography system of claim 7 wherein the display provides at least one illuminated indicator positioned proximate to the location to indicate through illumination and its proximity, the location information.

9. An x-ray computed tomography system comprising:
   an x-ray source for projecting a beam of x-rays toward a patient at different angles about a patient over an angular range;
   an x-ray detector providing multiple detector elements positioned to measure attenuation of the x-rays of the beams by the patient passing through the patient at the different angles over the angular range; and
   an electronic computer communicating with the x-ray source and x-ray detector to:
   (a) receive location information about a location of a nonpatient proximate to the x-ray computed tomography system;
   (b) based on the location information, control the x-ray source to preferentially direct x-rays through the patient toward the location to acquire a tomographic projection set of x-ray attenuation by the patient; and (c) reconstruct a tomographic image from measured attenuation of the preferentially directed x-rays;
wherein the electronic computer outputs an estimate of scatter dose received at the location according to the preferentially directed x-rays;
further including a radiation sensor positioned proximate to the location for determining an actual scatter dose and wherein the electronic computer compares the actual scatter dose to the estimate of scatter dose to provide a warning if these differ by more than a predetermined amount.

10. An x-ray computed tomography system comprising:
an x-ray source for projecting a beam of x-rays toward a patient at different angles about a patient over an angular range;
an x-ray detector providing multiple detector elements positioned to measure attenuation of the x-rays of the beams by the patient passing through the patient at the different angles over the angular range; and
an electronic computer communicating with the x-ray source and x-ray detector to:
(a) receive location information about a location of a nonpatient proximate to the x-ray computed tomography system;
(b) based on the location information, control the x-ray source to preferentially direct x-rays through the patient toward the location to acquire a tomographic projection set of x-ray attenuation by the patient; and
(c) reconstruct a tomographic image from measured attenuation of the preferentially directed x-rays;
wherein the electronic computer further receives patient positioning information indicating a positioning of the patient in the x-ray computed tomography system and preferentially directs x-rays through the patient toward the location based on the location information and patient positioning information.

11. The x-ray computed tomography system of claim 10 wherein the preferential direction of x-rays based on location information and the patient positioning information minimizes a joint function of patient dose and nonpatient dose at the location.

12. An x-ray computed tomography system comprising:
an x-ray source for projecting a beam of x-rays toward a patient at different angles about a patient over an angular range;
an x-ray detector providing multiple detector elements positioned to measure attenuation of the x-rays of the beams by the patient passing through the patient at the different angles over the angular range; and
an electronic computer communicating with the x-ray source and x-ray detector to:
(a) receive location information about a location of a nonpatient proximate to the x-ray computed tomography system;
(b) based on the location information, control the x-ray source to preferentially direct x-rays through the patient toward the location to acquire a tomographic projection set of x-ray attenuation by the patient; and
(c) reconstruct a tomographic image from measured attenuation of the preferentially directed x-rays;
wherein the electronic computer further receives information describing a location of a probe inserted into the patient and preferentially directs x-rays through the patient toward the location based on the location information and the location of the patient-inserted probe to reduce probe-induced image artifacts.

13. An x-ray computed tomography system comprising:
an x-ray source for projecting a beam of x-rays toward a patient at different angles about a patient over an angular range;
an x-ray detector providing multiple detector elements positioned to measure attenuation of the x-rays of the beams by the patient passing through the patient at the different angles over the angular range; and
an electronic computer communicating with the x-ray source and x-ray detector to:
(a) receive location information about a location of a nonpatient proximate to the x-ray computed tomography system;
(b) based on the location information, control the x-ray source to preferentially direct x-rays through the patient toward the location to acquire a tomographic projection set of x-ray attenuation by the patient; and
(c) reconstruct a tomographic image from measured attenuation of the preferentially directed x-rays;
wherein the electronic computer further receives information about a location of an x-ray shield proximate to the location and preferentially directs x-rays through the patient toward the location based on location information and shield location.

14. An x-ray computed tomography system comprising:
an x-ray source for projecting a beam of x-rays toward a patient at different angles about a patient over an angular range;
an x-ray detector providing multiple detector elements positioned to measure attenuation of the x-rays of the beams by the patient passing through the patient at the different angles over the angular range; and
an electronic computer communicating with the x-ray source and x-ray detector to:
(a) receive location information about a location of a nonpatient proximate to the x-ray computed tomography system;
(b) based on the location information, control the x-ray source to preferentially direct x-rays through the patient toward the location to acquire a tomographic projection set of x-ray attenuation by the patient; and
(c) reconstruct a tomographic image from measured attenuation of the preferentially directed x-rays:
wherein the electronic computer further operates to display a tomographic image of the patient modified by simulated noise according to a selected x-ray fluence of the x-ray source and to receive an input allowing physician adjustment of the selected x-ray fluence and further controls the x-ray source to provide a fluence matching the selected x-ray fluence during the preferential direction of x-rays through the patient toward the location.

15. A method of interventional computed tomography fluoroscopy using an x-ray computed tomography system having:
an x-ray source for projecting a beam of x-rays toward a patient at different angles about a patient over an angular range;
an x-ray detector providing multiple detector elements positioned to measure attenuation of the x-rays of the beams by the patient passing through the patient at the different angles over the angular range; and
an electronic computer communicating with the x-ray source and x-ray detector to: receive location information about a location of a nonpatient proximate to the x-ray computed tomography system; perform a scatter simulation based on patient information and the received location; based on the scatter simulation, control the x-ray source to preferentially direct x-rays through the patient toward the location to acquire a tomographic projection set of x-ray attenuation by the patient; and reconstruct a tomographic image from measured attenuation of the preferentially directed x-rays; the method comprising the steps of:

(a) providing information about the location of a nonpatient individual with respect to the x-ray computed tomography system;

(b) performing a scatter simulation based on the received location and patient information; and (c) based on the scatter simulation, providing a signal to the x-ray computed tomography system to control the x-ray source to preferentially direct x-rays through the patient toward the location to obtain a tomographic projection set and to reconstruct and display a corresponding tomographic image.

16. The method of claim 15 further including repeating steps (a)-(c) in between adjustments of a medical device within the patient by the nonpatient individual and captured by the tomographic images.

* * * * *